United States Patent
Frimerman et al.

(10) Patent No.: US 7,160,240 B2
(45) Date of Patent: Jan. 9, 2007

(54) CONTROL OF BODY ELECTRICAL ACTIVITY BY MAGNETIC FIELDS

(75) Inventors: Aaron Frimerman, Tel Aviv (IL); Eshel Ben-Jacob, Tel Aviv (IL)

(73) Assignee: Ramot At Tel Aviv University Ltd., Tel Aviv (IL)

( * ) Notice: Subject to any disclaimer, the term of this patent is extended or adjusted under 35 U.S.C. 154(b) by 580 days.

(21) Appl. No.: 10/467,505

(22) PCT Filed: Feb. 7, 2002

(86) PCT No.: PCT/IB02/00362

§ 371 (c)(1),
(2), (4) Date: Dec. 3, 2003

(87) PCT Pub. No.: WO02/062283

PCT Pub. Date: Aug. 15, 2002

(65) Prior Publication Data

US 2004/0077923 A1    Apr. 22, 2004

Related U.S. Application Data

(60) Provisional application No. 60/267,140, filed on Feb. 8, 2001.

(51) Int. Cl.
*A61N 1/00*    (2006.01)
(52) U.S. Cl. ......................................................... 600/13
(58) Field of Classification Search ............... 600/9–15
See application file for complete search history.

(56) References Cited

U.S. PATENT DOCUMENTS

| | | | |
|---|---|---|---|
| 4,022,701 A | 5/1977 | Sawa et al. |
| 4,056,097 A | 11/1977 | Maass |
| 4,678,616 A | 7/1987 | Kawashima |
| 4,723,536 A | 2/1988 | Rauscher et al. |
| 5,160,447 A | 11/1992 | Ishikawa et al. |
| 5,170,784 A | 12/1992 | Ramon et al. |

OTHER PUBLICATIONS

Ronen Segev, et al, "Hidden Neuronal Correlations: A Possible Template for Information Storage", School of Physics and Astronomy, Faculty of Exact Sciences, Tel Aviv Unviersity, Jun. 11, 2003.
Ronen Segev, et al, "Formation of Electrically Active Clusterized Neural Networks", Physical Review Letters, vol. 90, No. 16, Apr. 25, 2003.

*Primary Examiner*—John P. Lacyk
(74) *Attorney, Agent, or Firm*—Ladas & Parry LLP

(57) ABSTRACT

Apparatus (40) for generating a localized magnetic field inside a body of a living subject (44) includes first and second electromagnets (46,48), adapted to be positioned in proximity to the body so as to apply magnetic fields thereto. The core (50) of at least one of the electromagnets has a shape that can be altered under control of an operator of the apparatus so as to adjust the magnetic fields to assume a desired relation within the body.

28 Claims, 5 Drawing Sheets

CONTROL OF BODY ELECTRICAL ACTIVITY BY MAGNETIC FIELDS

CROSS-REFERENCE TO RELATED APPLICATION

This application claims the benefit of U.S. Provisional Patent Application No. 60/267,140, filed Feb. 8, 2001, which is incorporated herein by reference.

FIELD OF THE INVENTION

The present invention relates generally to devices and methods for generating magnetic fields in living body tissues, and specifically to devices and methods for inducing electrical pulses in body tissues by targeted electromagnetic radiation.

BACKGROUND OF THE INVENTION

A wide scope of human diseases and medical conditions are amenable to treatment by electric pulses delivered to specific areas of internal bodily organs or cells. Conditions that have been treated in this fashion include cardiac diseases, disorders of the brain (neurological and psychiatric), conditions of the spinal cord and peripheral nerves, and muscular disorders, to mention just a few.

In conditions of heart disease, such as acute myocardial infarction (MI), for example, the heart may go into ventricular fibrillation (VF). VF is typically treated by a prompt delivery of direct-current (DC) electrical shock to the patient's chest, known as defibrillation. In less acute disease conditions, cardiac arrhythmias may occur that require application of a milder DC shock for cardioversion. For extended treatment of arrhythmias, an artificial pacemaker is commonly used to control the heart rate. For this purpose, a suitable electrode is typically inserted into the heart by means of a catheter passed through the patient's venous system.

External defibrillation devices are typically based on discharge of a high-voltage, high-energy pulse (360 Joules for VF) from a capacitor. The strong pulse is needed in order to overcome the electrical resistance of body tissues and provide a sufficient stimulus to the patient's heart. To deliver the DC shock, a skilled operator smears a conductive protective gel on two large paddles and places them properly on the patient's chest, one over the heart base, the second over the heart apex. The operator ensures that no one is touching the patient, and then presses a button on each paddle to discharge the pulse into patient's chest. The results are typically observed on a electrocardiograph (ECG). As the electrical energy is only crudely directed to the heart, this routine may have to be repeated several times before the normal heart rhythm is recovered. This procedure causes trauma to the patient and entails a risk of severe electric shock to the treating personnel.

Attempts have been made to deliver electrical currents directly to the human heart or other internal body organs without surgical invasion or external electrical contacts, by applying a varying magnetic field to the body. For example, U.S. Pat. No. 4,723,536, whose disclosure is incorporated herein by reference, describes a device for heart pacemaking and pain reduction using external magnetic fields. An electromagnet comprising a wire coil is applied to the patient's body adjacent to the heart (for pacemaking) or to the head (for pain reduction). An alternating electrical current is applied to the coil in order to generate the desired magnetic field. The inventors indicate that the magnetic field intensity at the poles of the electromagnet that is needed in order to pace a human heart is 0.5 to 2.0 Gauss.

U.S. Pat. No. 5,170,784, whose disclosure is also incorporated herein by reference, describes a magnetic cardiac pacemaker using biphasic pulses of mixed frequencies and waveforms that are applied to a field coil, in order to generate magnetic pulses of relatively low intensity (less than 200 Gauss) without the use of leads. The device can be worn externally on the chest near the heart to enable the magnetic field to penetrate the body and control the heart muscle as a non-invasive cardiac pacemaker, or it can be inserted subcutaneously for long-term pacing.

U.S. Pat. No. 4,056,097, whose disclosure is likewise incorporated herein by reference, describes a contactless electromagnetic stimulus transducer, made of two curved ferromagnetic pole pieces with electric coils wound thereon. The pole pieces are designed to encircle (at least partially) the chest or the head of the patient, and are hinged in order to allow the distance between them to be adjusted. The electric coils are connected in opposition, so that the pole pieces generate opposing magnetic fields in the patient's body.

SUMMARY OF THE INVENTION

It is an object of some aspects of the present invention to provide improved devices and methods for applying magnetic fields to internal body organs.

In preferred embodiments of the present invention, at least one electromagnet with a shapeable core is used to apply a magnetic field to target in the body, typically in an organ such as the heart. The core, preferably comprising a ferromagnetic material, may include one or more flexible joints, or it may alternatively be made of a flexible material, such as a deformable plastic with ferromagnetic properties. Typically, a pair of electromagnets are applied to opposing sides of the body, wherein one or both of the electromagnets have such flexible cores. An operator adjusts the positions and shapes of the cores so as to generate a focused magnetic field at the target. The windings of the electromagnets are preferably driven with alternating currents, most preferably pulsed currents, so that the magnetic field at the target is pulsed, as well. The pulsed magnetic field causes electrical current pulses to be generated in the tissue, for use in pacing or defibrillating the heart, for example, or for treatment or diagnosis of other body organs, such as the brain, nervous system or muscles.

The use of an electromagnet with a flexible core allows the operator to target and focus the magnetic field within the body with much greater precision than is afforded by methods for magnetic stimulation that are known in the art. Consequently, a higher magnetic flux is achieved on target, resulting in a stronger electrical current pulse in the tissue, and therefore more effective therapeutic or diagnostic stimulation.

There is therefore provided, in accordance with a preferred embodiment of the present invention, apparatus for generating a localized magnetic field inside a body of a living subject, the apparatus including:

a first electromagnet, including a first core and a first winding surrounding the first core, and adapted to be positioned in proximity to the body so as to apply a first magnetic field thereto;

a second electromagnet, including a second core and a second winding surrounding the second core, and adapted to be positioned in proximity to the body so as to apply a second magnetic field thereto, the second core having a shape that can be altered under control of an operator of the apparatus so as to adjust the second magnetic field to assume a desired relation to the first magnetic field; and driving circuitry, coupled to apply an electrical current to the first and second windings in order to generate the first and second magnetic fields.

Preferably, the electrical current includes a pulsed current, whereby application of the current to the windings causes the first and second magnetic fields in the body to be pulsed.

Further preferably, the second magnetic field is adjusted in the desired relation so as to generate a region of focused magnetic flux due to the first and second magnetic fields within the body. Most preferably, the first and second electromagnets are positioned and at least the second magnetic field is adjusted so that the focused magnetic flux causes an electrical potential to be generated in a selected organ of the body.

In a preferred embodiment, the selected organ includes a heart, and the first and second electromagnets are positioned and adjusted and the electrical current is controlled so that the electrical potential causes pacing of the heart. Alternatively, the first and second electromagnets are positioned and adjusted and the electrical current is controlled so that the electrical potential causes defibrillation of the heart. Preferably, the apparatus includes a device for observing performance of the heart and generating an output signal responsive thereto, wherein the first and second magnetic fields are adjusted responsive to the output signal.

Preferably, the shape of the first core can also be altered under control of the operator of the apparatus so as to adjust the first magnetic field.

There is also provided, in accordance with a preferred embodiment of the present invention, apparatus for generating a localized magnetic field inside a body of a living subject, the apparatus including:

an electrical winding, which is adapted to be driven by an electrical current so as to generate a magnetic field in the body; and a core, upon which the winding is wound, the core including at least first and second ferromagnetic sections and a joint that connects the sections one to another, such that the joint is adjustable under control of an operator of the apparatus so as to direct lines of flux of the magnetic field within the body.

There is additionally provided, in accordance with a preferred embodiment of the present invention, apparatus for generating a localized magnetic field inside a body of a living subject, the apparatus including:

an electrical winding, which is adapted to be driven by an electrical current so as to generate a magnetic field in the body; and a core, upon which the winding is wound, the core including a flexible ferromagnetic material, which is adapted to be bent under control of an operator of the apparatus so as to direct lines of flux of the magnetic field within the body.

Preferably, the flexible ferromagnetic material includes a deformable plastic matrix and particles of a ferromagnetic substance contained in the matrix. Alternatively, the flexible ferromagnetic material includes a deformable container, a fluid held within the container, and particles of a ferromagnetic substance suspended in the fluid. In a preferred embodiment, the core includes multiple lobes of the flexible ferromagnetic material, which are adapted to be bent individually to respective angles.

There is further provided, in accordance with a preferred embodiment of the present invention a method for generating a localized magnetic field inside a body of a living subject, the method including:

positioning a first electromagnet, including a first core and a first winding surrounding the first core, in proximity to the body so as to apply a first magnetic field thereto;

positioning a second electromagnet, including a second core and a second winding surrounding the second core, in proximity to the body so as to apply a second magnetic field thereto; and modifying a shape of at least one of the cores so that the first and second magnetic fields assume a desired relation one to another within the body.

In a preferred embodiment, the selected organ includes a heart, and the method includes observing performance of the heart and generating an output signal responsive thereto, wherein the first and second electromagnets are positioned and the shape of the at least one of the cores is modified responsive to the output signal.

The present invention will be more fully understood from the following detailed description of the preferred embodiments thereof, taken together with the drawings in which:

DETAILED DESCRIPTION OF PREFERRED EMBODIMENTS

Figure 1:
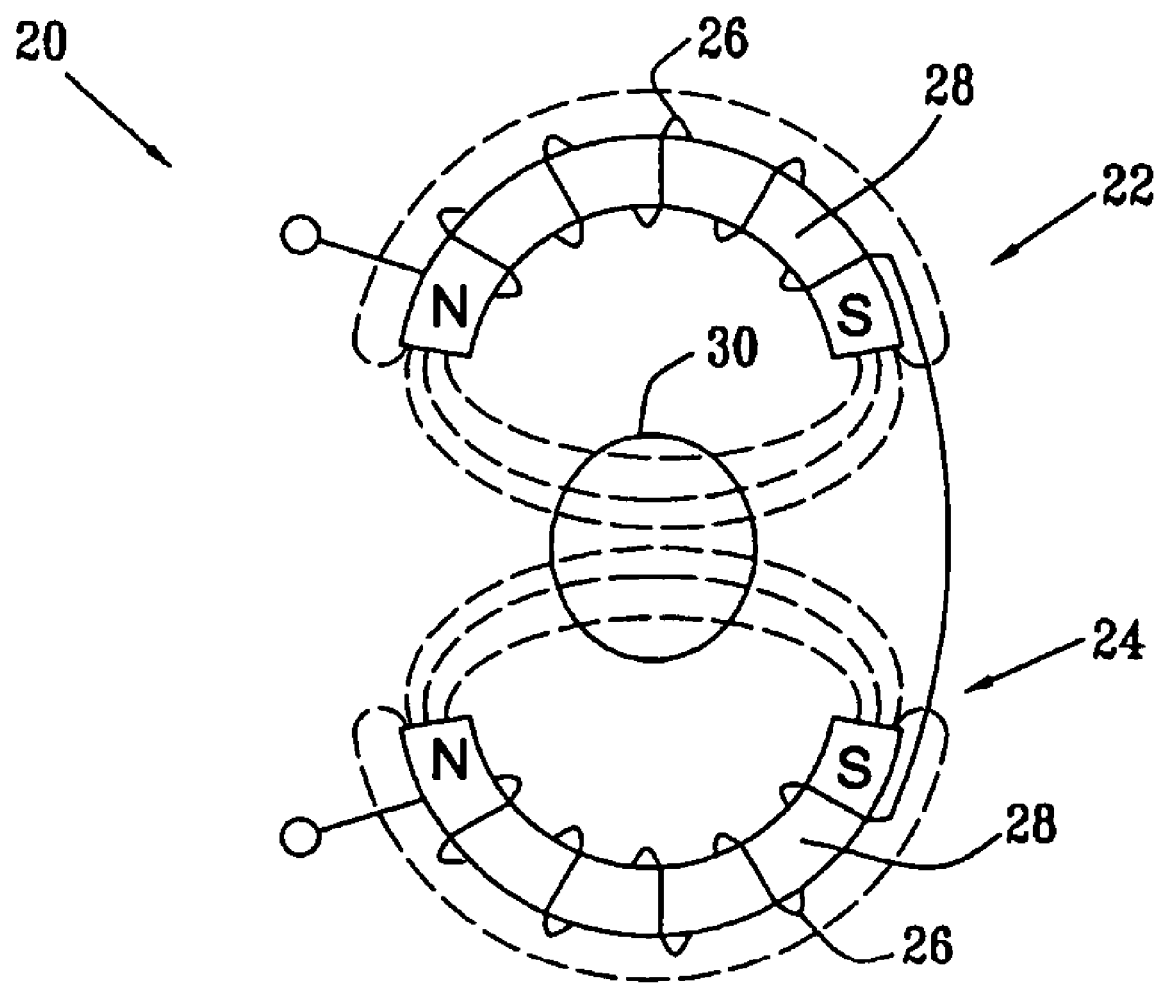
FIG. 1 is a schematic side view of apparatus for generating a focused magnetic field, as is known in the art.

FIG. 1 is a schematic side view of apparatus 20 for generating a focused magnetic field, as is known in the art. The apparatus comprises two electromagnets 22 and 24, having cylindrical inductive coils 26 wound around generally cylindrical ferromagnetic cores 28. The two coils are connected in opposition to a source of direct or alternating current (not shown). As a result, the north (N) and south (S) poles of the two coils are aligned, as shown in the figure. In the configuration of FIG. 1, cores 28 are curved, so that the magnetic fields are focused in a target zone 30 between the poles on the concave side of the cores. Within zone 30, the magnetic field intensity is generally strong and roughly uniform. It will be observed, however, that if the spacing or relative angle between electromagnets 22 and 24 changes significantly, the lines of magnetic field will no longer be focused in zone 30, and the strength and uniformity of the field in the zone will be adversely affected.

Figure 2A:
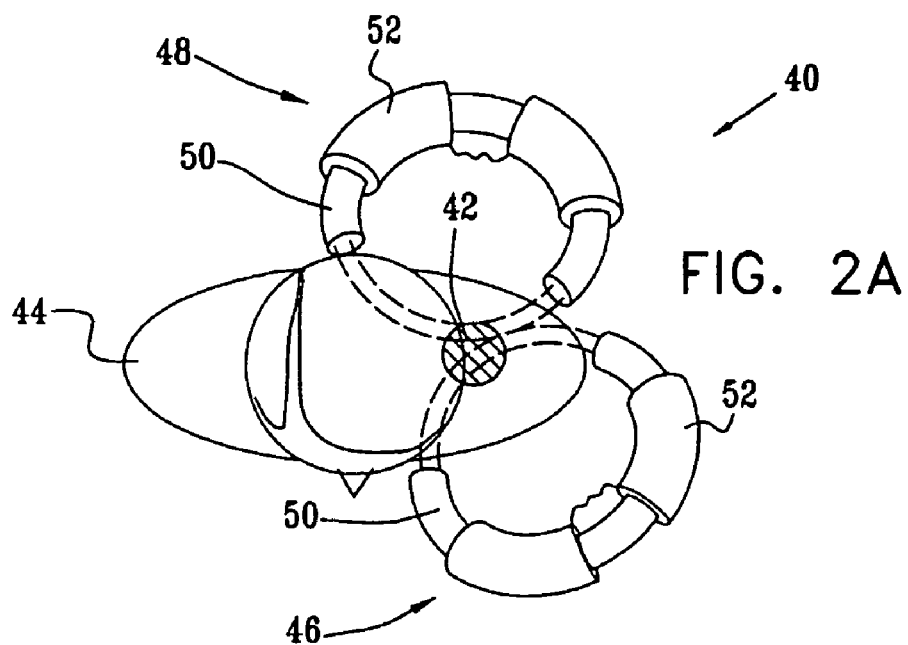
FIGS. 2A and 2B are schematic, pictorial, top and frontal views, respectively, of a system for applying magnetic stimulation to the heart of a subject, in accordance with a preferred embodiment of the present invention.
Figure 2B:
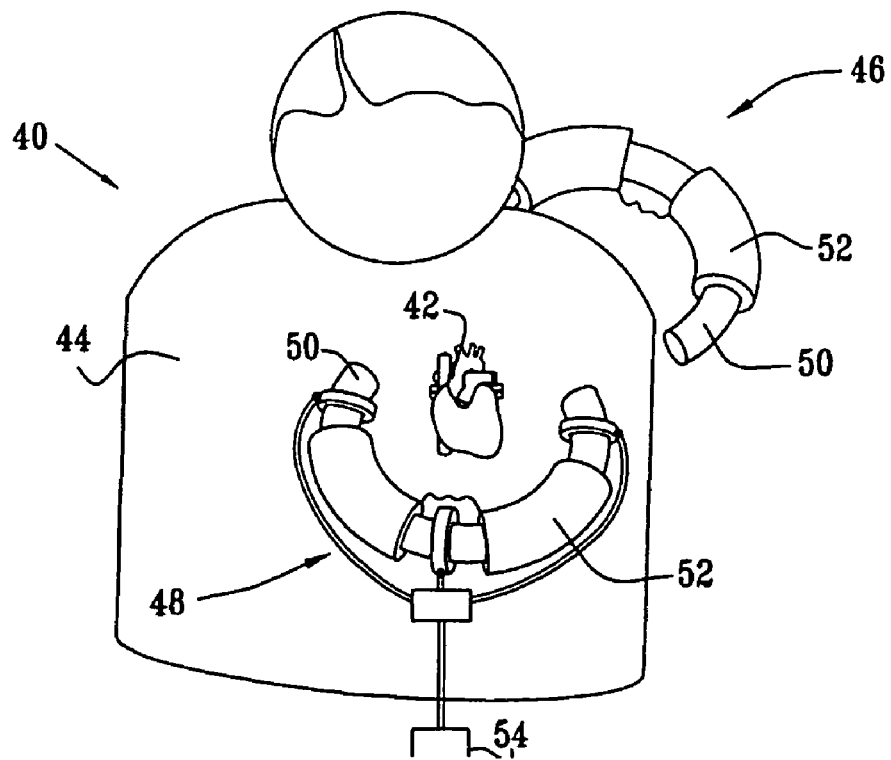

FIGS. 2A and 2B are schematic, pictorial illustrations of a system 40 for generating focused magnetic fields within a heart 42 of a human subject 44, in accordance with a preferred embodiment of the present invention. FIG. 2A is a top view of the system, while FIG. 2B is a frontal view, both showing the location of heart 42 within the subject's chest. A pair of electromagnets 46 and 48 are placed behind and in front of subject 44, respectively. Each of the electromagnets comprises a flexible core 50, on which a coil 52 is wound. Different types of cores may be used for this purpose. Some exemplary types are described with reference to the figures that follow. Coils 52 are connected in opposition to a current source, like coils 26 in FIG. 1, thereby generating a focused magnetic field in heart 42.

Cores 50 can be shaped by an operator of system 40, unlike cores 28 that are used in systems known in the art. Mounting devices 54, such as brackets or other suitable mounting hardware, are preferably provided in order to hold electromagnets 46 and 48 in the desired shape and place during treatment. (For simplicity of illustration, only the mounting device for electromagnet 48 is shown in the figures.) The operator can thus adjust the positions and orientations of electromagnets 46 and 48, together with the positions and bending angles of the cores, so that the lines of magnetic field are precisely focused in heart 42. Alternatively, mounting devices 54 may be electromechanically controlled, and may be capable of adjusting the positions and angles automatically.

Generally speaking, the operator or automated control system draws the poles of the electromagnets closer together or farther apart, and changes the relative angles of the poles, depending on the size and shape of the subject's body and the location of the organ in which the magnetic field is to be focused. Electromagnets 46 and 48 may also be turned to different orientation angles, in order to control the angular orientation of the magnetic field lines in heart 42. Coils 52 are preferably driven by a pulsating electrical current, so as to generating a pulsed, focused magnetic field in the body. The pulsed magnetic field, in turn, induces electrical pulses in the tissue of heart 42, having amplitude, frequency and shape that depend on the amplitude, frequency and waveform of the current driving the coils. Further details regarding the use of system 40 in treating the heart, as well as other organs, are described hereinbelow with reference to FIG. 9.

Although only two electromagnets 46 and 48 are shown in FIGS. 2A and 2B, three or more electromagnets with flexible cores may be disposed around the body of subject 44, and may be shaped and aligned together to give a stronger, focused magnetic field in heart 42 or in another target location. A larger number of coils allows better stabilization, directing and focusing of the magnetic field but is harder to align and manipulate in practice. Alternatively, a single electromagnet with a flexible core may be used in some applications.

Figure 3A:
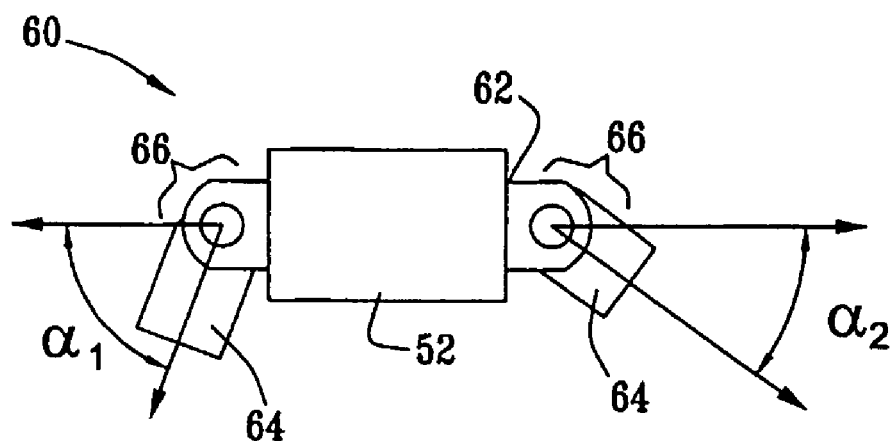
FIGS. 3A and 3B are schematic top and side views, respectively, of an electromagnet with a jointed core, in accordance with a preferred embodiment of the present invention.
Figure 3B:
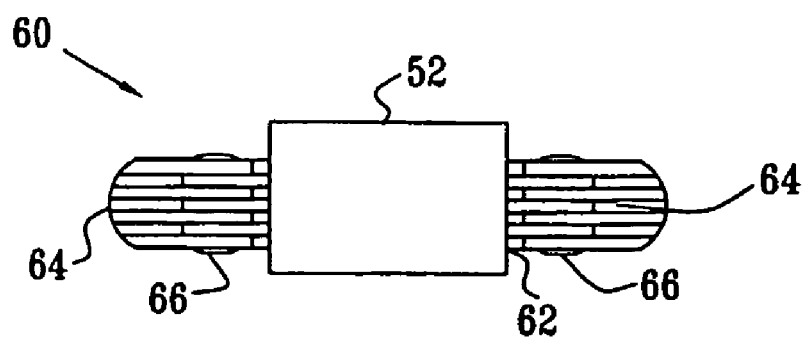

FIGS. 3A and 3B show an electromagnet 60 with cylindrical inductive coil 52 wound on a laminated core 62, in accordance with a preferred embodiment of the present invention. FIG. 3A is a top view (as seen in the perspective of FIG. 2A), while FIG. 3B is a side view. Core 62 is formed from parallel sheets of a suitable ferromagnetic material, as is known in the art. The core comprises a central part that is largely contained within coil 52, connected to two articulating extremities 64 by joints 66. The operative configuration of electromagnet 60 is characterized by two bending angles $\alpha_1$ and $\alpha_2$ formed between the axis of the central part and the axes of extremities 64. The two angles are independently adjustable by the operator, who then fixes the angles in place when the magnetic field is focused in the desired location.

Figure 4:
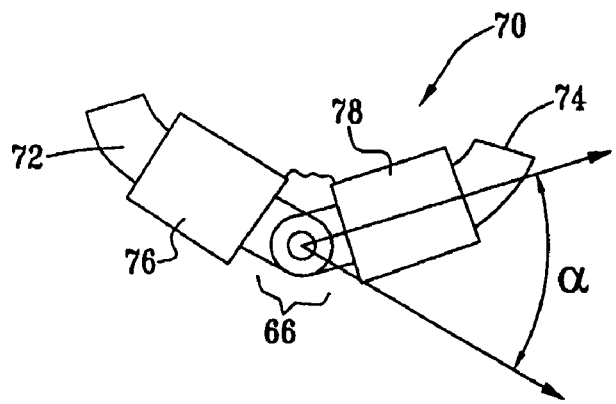
FIG. 4 is a schematic top view of an electromagnet with a jointed core, in accordance with another preferred embodiment of the present invention.

FIG. 4 is a schematic top view of another electromagnet 70 with an articulated core, in accordance with a preferred embodiment of the present invention. The core in this case comprises two arms 72 and 74, connected by joint 66. Arms 72 and 74 are wound with respective coils 76 and 78, which are connected so as to have the same current direction around the core. The operative configuration of this electromagnet is characterized by one angle $\alpha$ formed between the axes of arms 72 and 74.

Figure 5:
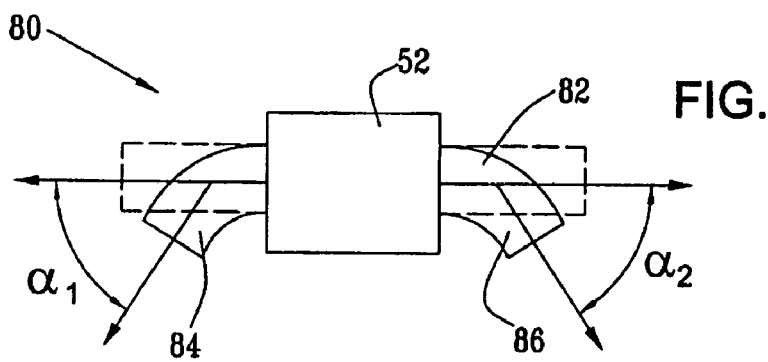
FIGS. 5–8 are schematic top views of electromagnets with cores made of flexible materials, in accordance with a number of preferred embodiments of the present invention.

FIG. 5 is a schematic top view of an electromagnet 80 whose core 82 is made of a flexible material, in accordance with a preferred embodiment of the present invention. Typically, core 82 comprises a composite ferromagnetic material, made of a ferromagnetic powder filler, for example, in a plastic base, such as a polymeric material, allowing the core to be deformed by the operator. Various methods are known in the art for making magnetic cores using ferromagnetic powders in a plastic matrix. Exemplary methods are described in U.S. Pat. Nos. 4,022,701, 4,678, 616 and 5,160,447, whose disclosures are incorporated herein by reference. Whereas the typical magnets described in these patents are mechanically stiff, the methods of manufacture described in these patents can easily be adapted to produce a flexible magnetic core, by mixing the ferromagnetic powder into a matrix of suitable flexible plastic material.

Alternatively, core 82 may be produced by suspending a ferromagnetic powder in a viscous fluid or other vehicle, and enclosing the suspension in a flexible tube that is adapted to preserve its deformed state.

In either case, the operator can bend extremities 84 and 86 so that they assume deformed positions characterized by respective angles $\alpha_1$ and $\alpha_2$. In this case, the angles are measured between the perpendiculars to the side faces of the extremities in their deformed and non-deformed positions (as shown by broken lines in FIG. 5)

Figure 6:
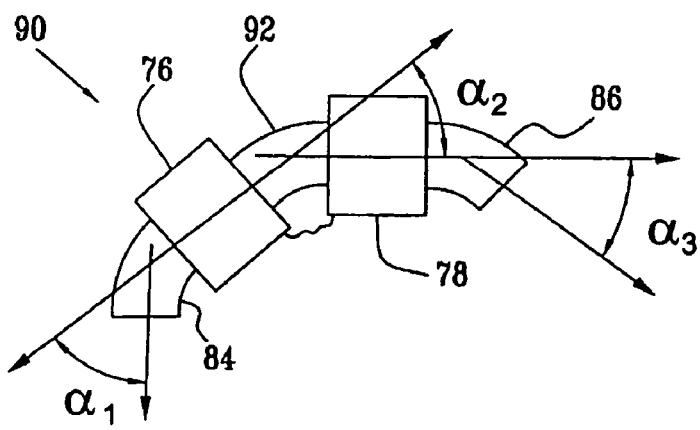

FIG. 6 is a schematic top view of an electromagnet 90, comprising dual inductive coils 76 and 78, with a deformable magnetic core 92, in accordance with a preferred embodiment of the present invention. Core extremities 84 and 86 can in this case be bent so that the operator is able to manipulate three angles: $\alpha_1$, $\alpha_2$ and $\alpha_3$.

Figure 7:
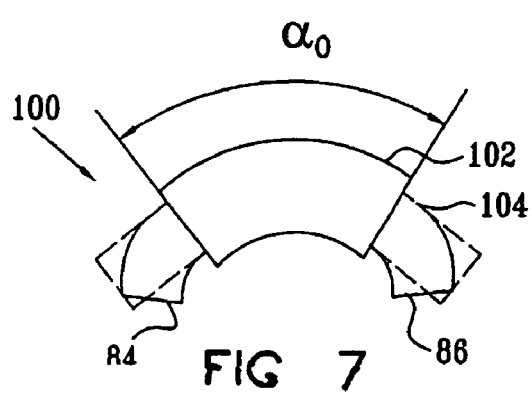

FIG. 7 is a schematic top view of an electromagnet 100, in accordance with another preferred embodiment of the present invention. In this embodiment, a coil 102 itself has a curved shape, corresponding to the curvature of the central part of core 104. As a result, the electromagnet is characterized by an initial bend angle $\alpha_0$. This is the type of coil that is used in electromagnets 46 and 48, shown in FIGS. 2A and 2B, and which may similarly be used in combination with substantially any of the core configurations shown in FIGS. 3–6. The operator of electromagnet 100 is able to bend extremities 84 and 86 in order to achieve the desired overall bend.

Figure 8:
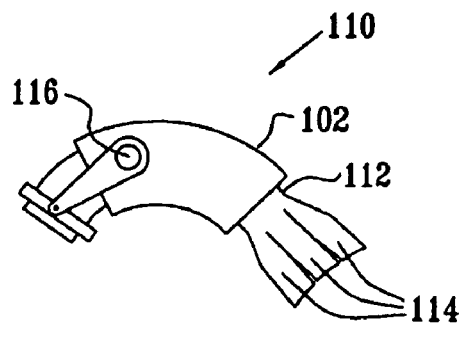

FIG. 8 is a schematic top view of an electromagnet 110, in accordance with yet another preferred embodiment of the present invention. As illustrated by this embodiment, the extremities of core 112 may have different shapes suitable for focusing of the magnetic field in different cases. For example, one or both extremities may be split into a number of individually-deformable lobes 114. Additionally or alternatively, if the material of the deformable core has some residual elasticity or does not stably maintain its deformed state for some other reason, a mechanical bracket 116 of non-magnetic material may be used to fix the core extremities at the desired angles.

Figure 9:
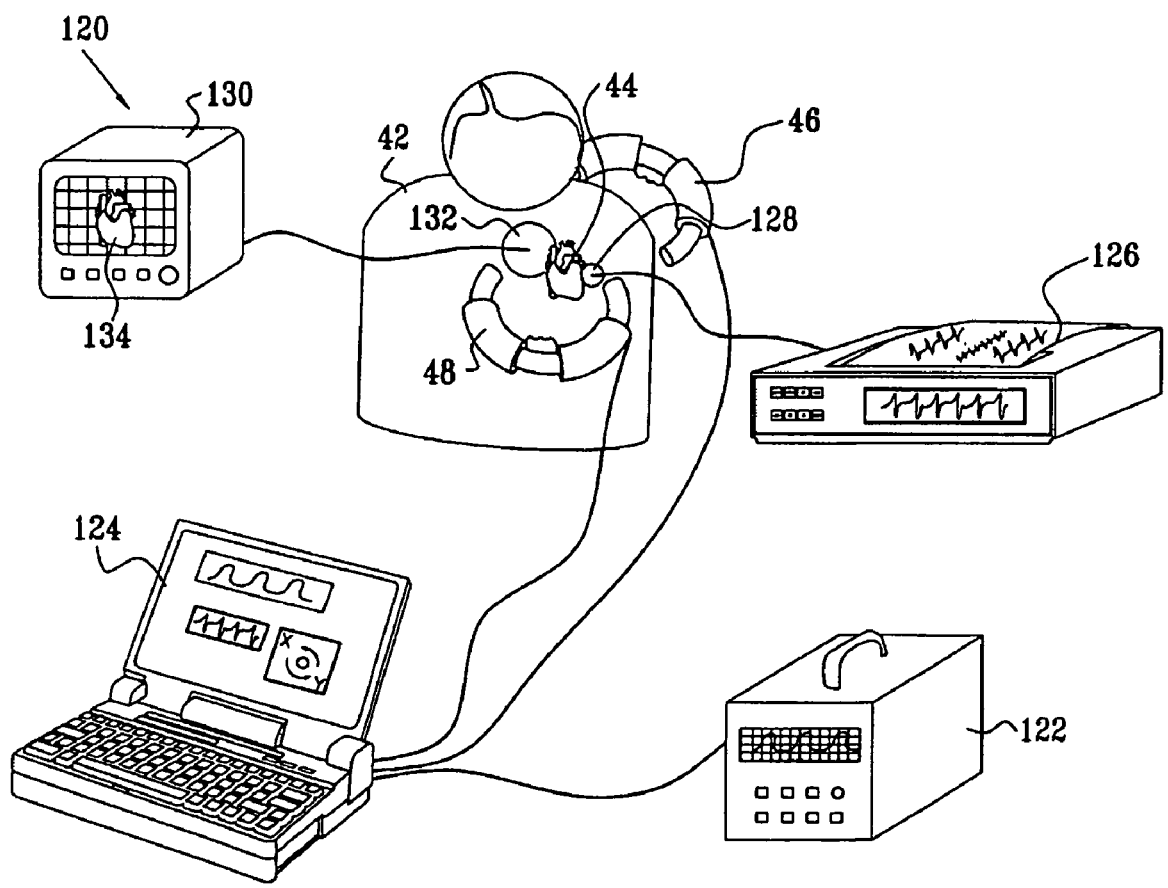
FIG. 9 is a schematic, pictorial illustration of a system for treatment of the heart using magnetic stimulation, in accordance with a preferred embodiment of the present invention.

FIG. 9 is a schematic, pictorial view of a computerized system 120 for generating a controlled magnetic field in heart 44, in accordance with a preferred embodiment of the present invention. Besides electromagnets 46 and 48 (as described above with reference to FIGS. 2A and 2B), the system comprises an electric waveform generator 122, a computer console 124, and an electrocardiograph (ECG) 126 with electrode 128. (Typically, multiple ECG electrodes are used, as is known in the art, but for the sake of simplicity, only one electrode is shown here.) ECG 126 is used to observe the electrical activity of heart 44 prior to treatment by system 120, and then to monitor the effect of the magnetic fields generated by the system on the heart. Optionally, an imaging device, such as an ultrasound echograph 130 with a transducer 132, is used to form an image 134 of heart 44. This image is useful both in accurately determining the position of the heart, and as a further means for observing the effect of the magnetic fields on the heart. Some or all of waveform generator 122, ECG 126 and echograph 130 may be merged with console 124 in a single, integrated unit.

Prior to treatment, console 124 preferably receives signal inputs from ECG 126 and echograph 130, as well as manual input from an operator of system 120. The console is programmed with software capable of determining, based on these inputs, the desired focal point of the magnetic fields in the body of subject 42, and the strength of the magnetic field to be generated there. Based on this determination, the console outputs a combination of treatment parameters, which typically include:

☐ Positions and orientations of electromagnets 46 and 48 relative to the body of subject 42.

☐ Shape parameters of the electromagnets, such as bending angles $\alpha_i$.

☐ Electrical current amplitude and waveform (and/or frequency) to be delivered from waveform generator 122 to the coils of the electromagnets.

These parameters may then be implemented manually by the operator, or they may be applied automatically by console 124, by controlling waveform generator 122 and mounting device 54 (FIG. 2B). The console or the operator may vary the parameters during treatment until the desired effect on the heart is observed.

In the configuration shown in FIG. 9, system 120 has a range of different applications, including:

Leadless electrical pacing of heart 44, without electrode insertion. The electrical pulse generated by the magnetic fields is directed, preferably by echocardiogram imaging, to a pre-selected target in the heart. Typically, pulsed magnetic fields between 0.01 and 0.1 tesla are sufficient to pace the heart, although other field strength values may also be used.

Directed electrical shock to the heart muscle to induce cardioversion and/or defibrillation, for treatment of more severe heart rhythm disturbances. Typically, magnetic fields of roughly 1 tesla are sufficient to defibrillate the heart, although here, too, other field strength values may also be used.

Non-invasive cardiac electro-physiological study. Electromagnets 46 and 48 induce stimulating electrical pulses to specific locations in the heart without insertion of electrodes. The response of the heart to the stimuli is recorded by ECG 126 and/or echograph 130. The type and focus of treatment subsequent to the study is determined by the ECG and/or echographic response pattern.

Non-invasive electrical ablation of abnormal sites in the heart. Such sites typically interfere with the heart's normal pulse generation or pulse conduction system and thus cause abnormalities in the heart rhythm. A focused, pulsed magnetic field of sufficient strength will induce a local electrical pulse in the heart that is capable of ablating the abnormal site, thus alleviating the heart rhythm disturbance.

In addition, system 120 may be configured to administer other types of treatment, to other areas of the body, including:

Magnetic stimulation of the brain, for indications including depression, as well as other neurological and psychiatric disorders.

Treatment of neurological (and particularly neuromuscular) disorders, using magnetic fields to induce electrical pulses in the spinal cord and peripheral nerves.

Treatment of muscular disorders, using magnetic fields applied directly in the muscles.

Although the preferred embodiments described hereinabove refer to certain exemplary types of flexible ferromagnetic cores and applicable windings, other shapeable core and winding configurations will be apparent to those skilled in the art and are considered to be within the scope of the present invention. Similarly, whereas certain particular therapeutic and diagnostic applications of systems 40 and 120 are shown and described above, the principles of the present invention may be applied to substantially any method of treatment or diagnosis that uses targeted magnetic fields within the body.

It will therefore be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for generating a localized magnetic field inside a body of a living subject, the apparatus comprising:
a first electromagnet, comprising a first core and a first winding surrounding the first core, and adapted to be positioned in proximity to the body so as to apply a first magnetic field thereto;
a second electromagnet, comprising a second core and a second winding surrounding the second core, and adapted to be positioned in proximity to the body so as to apply a second magnetic field thereto, the second core having a shape that can be altered under control of an operator of the apparatus so as to adjust the second magnetic field to assume a desired relation to the first magnetic field; and
driving circuitry, coupled to apply an electrical current to the first and second windings in order to generate the first and second magnetic fields.

2. Apparatus according to claim 1, wherein the electrical current comprises a pulsed current, whereby application of the current to the windings causes the first and second magnetic fields in the body to be pulsed.

3. Apparatus according to claim 1, wherein the second magnetic field is adjusted in the desired relation so as to generate a region of focused magnetic flux due to the first and second magnetic fields within the body.

4. Apparatus according to claim 3, wherein the first and second electromagnets are positioned and at least the second magnetic field is adjusted so that the focused magnetic flux causes an electrical potential to be generated in a selected organ of the body.

5. Apparatus according to claim 4, wherein the selected organ comprises a heart.

6. Apparatus according to claim 5, wherein the first and second electromagnets are positioned and adjusted, and wherein the electrical current is controlled so that the electrical potential causes pacing of the heart.

7. Apparatus according to claim 5, wherein the first and second electromagnets are positioned and adjusted, and wherein the electrical current is controlled so that the electrical potential causes defibrillation of the heart.

8. Apparatus according to claim 5, and comprising a device for observing performance of the heart and generating an output signal responsive thereto, wherein the first and second magnetic fields are adjusted responsive to the output signal.

9. Apparatus according to claim 1, wherein the shape of the first core can be altered under control of the operator of the apparatus so as to adjust the first magnetic field.

10. Apparatus according to claim 1, wherein at least the second core comprises at least first and second ferromagnetic sections and a joint that connects the sections one to another, so as to permit adjustment of an angular relation of the segments.

11. Apparatus according to claim 1, wherein at least the second core comprises a flexible ferromagnetic material, which is adapted to be bent so as to permit adjustment of an angular configuration of the core.

12. Apparatus for generating a localized magnetic field inside a body of a living subject, the apparatus comprising:
an electrical winding, which is adapted to be driven by an electrical current so as to generate a magnetic field in the body; and
a core, upon which the winding is wound, the core comprising at least first and second ferromagnetic sections and a joint that connects the sections one to another, such that the joint is adjustable under control of an operator of the apparatus so as to direct lines of flux of the magnetic field within the body.

13. Apparatus for generating a localized magnetic field inside a body of a living subject, the apparatus comprising:
an electrical winding, which is adapted to be driven by an electrical current so as to generate a magnetic field in the body; and
a core, upon which the winding is wound, the core comprising a flexible ferromagnetic material, which is adapted to be bent under control of an operator of the apparatus so as to direct lines of flux of the magnetic field within the body.

14. Apparatus according to claim 13, wherein the flexible ferromagnetic material comprises a deformable plastic matrix and particles of a ferromagnetic substance contained in the matrix.

15. Apparatus according to claim 13, wherein the flexible ferromagnetic material comprises:
a deformable container;
a fluid held within the container; and
particles of a ferromagnetic substance suspended in the fluid.

16. Apparatus according to claim 13, wherein the core comprises multiple lobes of the flexible ferromagnetic material, which are adapted to be bent individually to respective angles.

17. A method for generating a localized magnetic field inside a body of a living subject, the method comprising:
positioning a first electromagnet, comprising a first core and a first winding surrounding the first core, in proximity to the body so as to apply a first magnetic field thereto;
positioning a second electromagnet, comprising a second core and a second winding surrounding the second core, in proximity to the body so as to apply a second magnetic field thereto; and
modifying a shape of at least one of the cores so that the first and second magnetic fields assume a desired relation one to another within the body.

18. A method according to claim 17, and comprising driving the first and second windings with a pulsed current, so that the first and second magnetic fields in the body comprise pulsed fields.

19. A method according to claim 17, wherein modifying the shape comprises adjusting the shape of the at least one of the cores so as to generate a region of focused magnetic flux due to the first and second magnetic fields within the body.

20. A method according to claim 19, wherein the first and second electromagnets are positioned and the shape of the at least one of the cores is modified so that the focused magnetic flux causes an electrical potential to be generated in a selected organ of the body.

21. A method according to claim 20, wherein the selected organ comprises a heart.

22. A method according to claim 21, and comprising driving the first and second windings with a current having an amplitude and waveform selected so that the electrical potential causes pacing of the heart.

23. A method according to claim 21, and comprising driving the first and second windings with a current having an amplitude and waveform selected so that the electrical potential causes defibrillation of the heart.

24. A method according to claim 21, and comprising observing performance of the heart and generating an output signal responsive thereto, wherein the first and second electromagnets are positioned and the shape of the at least one of the cores is modified responsive to the output signal.

25. A method according to claim 17, wherein modifying the shape comprises varying an angle of a joint that connects first and second sections of the at least one of the cores one to another.

26. A method according to claim 17, wherein the at least the one of the cores comprises a flexible ferromagnetic material, and wherein modifying the shape comprises bending the core.

27. Apparatus according to claim 4, wherein the selected organ comprises at least one of a brain, a nerve and a muscle.

28. A method according to claim 20, wherein the selected organ comprises at least one of a brain, a nerve and a muscle.

* * * * *